US010602961B2

(12) United States Patent
Hirose et al.

(10) Patent No.: US 10,602,961 B2
(45) Date of Patent: Mar. 31, 2020

(54) RESPIRATION RATE DETERMINING APPARATUS, RESPIRATION RATE DETERMINING METHOD, AND PROGRAM RECORDING MEDIUM

(71) Applicant: Panasonic Intellectual Property Management Co., Ltd., Osaka (JP)

(72) Inventors: Yoshifumi Hirose, Kyoto (JP); Shoichi Araki, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 136 days.

(21) Appl. No.: 15/716,907

(22) Filed: Sep. 27, 2017

(65) Prior Publication Data

US 2018/0035916 A1 Feb. 8, 2018

Related U.S. Application Data

(63) Continuation of application No. PCT/JP2016/004681, filed on Oct. 25, 2016.

(30) Foreign Application Priority Data

Jan. 29, 2016 (JP) .................. 2016-015230

(51) Int. Cl.
*A61B 5/08* (2006.01)
*A61B 5/113* (2006.01)
*A61B 5/00* (2006.01)

(52) U.S. Cl.
CPC .......... *A61B 5/0816* (2013.01); *A61B 5/0022* (2013.01); *A61B 5/113* (2013.01);
(Continued)

(58) Field of Classification Search
CPC ..... A61B 5/0816; A61B 5/0022; A61B 5/113; A61B 5/6804; A61B 5/7257; A61B 5/7278
(Continued)

(56) References Cited

U.S. PATENT DOCUMENTS 6,081,742 A * 6/2000 Amano ................ A61B 5/0205
600/484
2005/0113711 A1 5/2005 Nakatani et al.
(Continued)

FOREIGN PATENT DOCUMENTS

JP 2005-198781 7/2005
JP 2006-247374 9/2006
(Continued)

OTHER PUBLICATIONS

International Search Report dated Dec. 27, 2016 in corresponding International Application No. PCT/JP2016/004681.

*Primary Examiner* — Daniel L Cerioni
(74) *Attorney, Agent, or Firm* — Wenderoth, Lind & Ponack, L.L.P.

(57) ABSTRACT

A respiration rate determining apparatus includes: an obtaining unit which obtains accelerations in directions that are mutually different, the accelerations being obtained by an acceleration sensor measuring a body movement by respiration of a user; a transform unit which transforms the accelerations in the directions obtained by the obtaining unit, into spectrum information items in a frequency domain; a phase removing unit which transforms the spectrum information items into amplitude spectra by removing phase information from the spectrum information items; a peak detector which adds up the amplitude spectra and detects a peak frequency based on an amplitude spectrum resulting from the adding up, the peak frequency indicating a respiratory component; and a respiration rate calculator which calculates a respiration rate using the peak frequency.

6 Claims, 11 Drawing Sheets

(52) U.S. Cl.
CPC .......... *A61B 5/6804* (2013.01); *A61B 5/7257* (2013.01); *A61B 5/7278* (2013.01); *A61B 2562/0219* (2013.01)

(58) Field of Classification Search
USPC ........................................................ 600/529
See application file for complete search history.

(56) References Cited

U.S. PATENT DOCUMENTS

| | | | |
|---|---|---|---|
| 2009/0062628 A1 | 3/2009 | Yamamoto et al. | |
| 2010/0286522 A1* | 11/2010 | Beach ................ | A61B 5/02007 600/441 |
| 2012/0065524 A1 | 3/2012 | Morren et al. | |
| 2012/0296221 A1 | 11/2012 | Morren | |
| 2016/0007864 A1* | 1/2016 | Scharf .................. | A61B 5/6814 600/301 |
| 2018/0078174 A1* | 3/2018 | Chan ........................ | A61B 5/08 |
| 2018/0333064 A1* | 11/2018 | Ogasawara .......... | A61B 5/0456 |

FOREIGN PATENT DOCUMENTS

| | | |
|---|---|---|
| JP | 2012-528657 | 11/2012 |
| JP | 2013-519421 | 5/2013 |
| WO | 2010/140130 | 12/2010 |
| WO | 2011/098944 | 8/2011 |

\* cited by examiner

RESPIRATION RATE DETERMINING APPARATUS, RESPIRATION RATE DETERMINING METHOD, AND PROGRAM RECORDING MEDIUM

CROSS REFERENCE TO RELATED APPLICATIONS

This application is a U.S. continuation application of PCT International Patent Application Number PCT/JP2016/004681 filed on Oct. 25, 2016, claiming the benefit of priority of Japanese Patent Application Number 2016-015230 filed on Jan. 29, 2016, the entire contents of which are hereby incorporated by reference.

BACKGROUND

1. Technical Field

The present disclosure relates to a respiration rate determining apparatus and a respiration rate determining method, and a program recording medium which determine a respiration rate based on measurement data of an acceleration sensor attached to the body of a person.

2. Description of the Related Art

Patent Literature (PTL) 1 (Japanese Unexamined Patent Application Publication No. 2006-247374) discloses a respiration rate determining apparatus which determines a respiration rate based on an acceleration sensor attached to the body of a person. Specifically, the respiration rate determining apparatus combines accelerations measured by a triaxial acceleration sensor attached to the body, and determines a respiration rate based on the frequency characteristics of the synthetic acceleration. This makes it possible to determine a respiration rate even when respiratory components included in the measured accelerations disperse into axes.

SUMMARY

After the acceleration sensor is attached to the chest of a user, the respiration rate determining apparatus of PTL 1 makes it possible to detect a chest movement when the user respires. Unfortunately, false detection may happen depending on a state of the user such as a posture.

The present disclosure provides a respiration rate determining apparatus capable of stably and accurately determining a respiration rate of a user regardless of a state of the user.

A respiration rate determining apparatus according to the present disclosure includes: an obtaining unit which obtains accelerations in directions that are mutually different, the accelerations being obtained by an acceleration sensor measuring a body movement by respiration of a user; a transform unit which transforms the accelerations in the directions obtained by the obtaining unit, into spectrum information items in a frequency domain; a phase removing unit which transforms the spectrum information items into amplitude spectra by removing phase information from the spectrum information items; a peak detector which adds up the amplitude spectra and detects a peak frequency based on an amplitude spectrum resulting from the adding up, the peak frequency indicating a respiratory component; and a respiration rate calculator which calculates a respiration rate using the peak frequency.

The respiration rate determining apparatus in the present disclosure is capable of accurately determining a respiration rate regardless of a state of the user such as a posture.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

DETAILED DESCRIPTION OF THE EMBODIMENTS

Hereinafter, embodiments will be described in detail with reference to the drawings. However, unnecessarily detailed descriptions may be omitted. For example, detailed descriptions of well-known matters or descriptions of components that are substantially the same as components previously described may be omitted. This is to avoid unnecessary redundancy and provide easily read descriptions for a person skilled in the art.

It should be noted that the appended drawings and the following descriptions are provided to facilitate sufficient understanding of the present disclosure for a person skilled in the art, and are not intended to limit the subject matter of the claims.

Embodiment 1

Hereinafter, Embodiment 1 will be described with reference to FIG. 1 through FIG. 12.

1-1. Configuration

Figure 1:
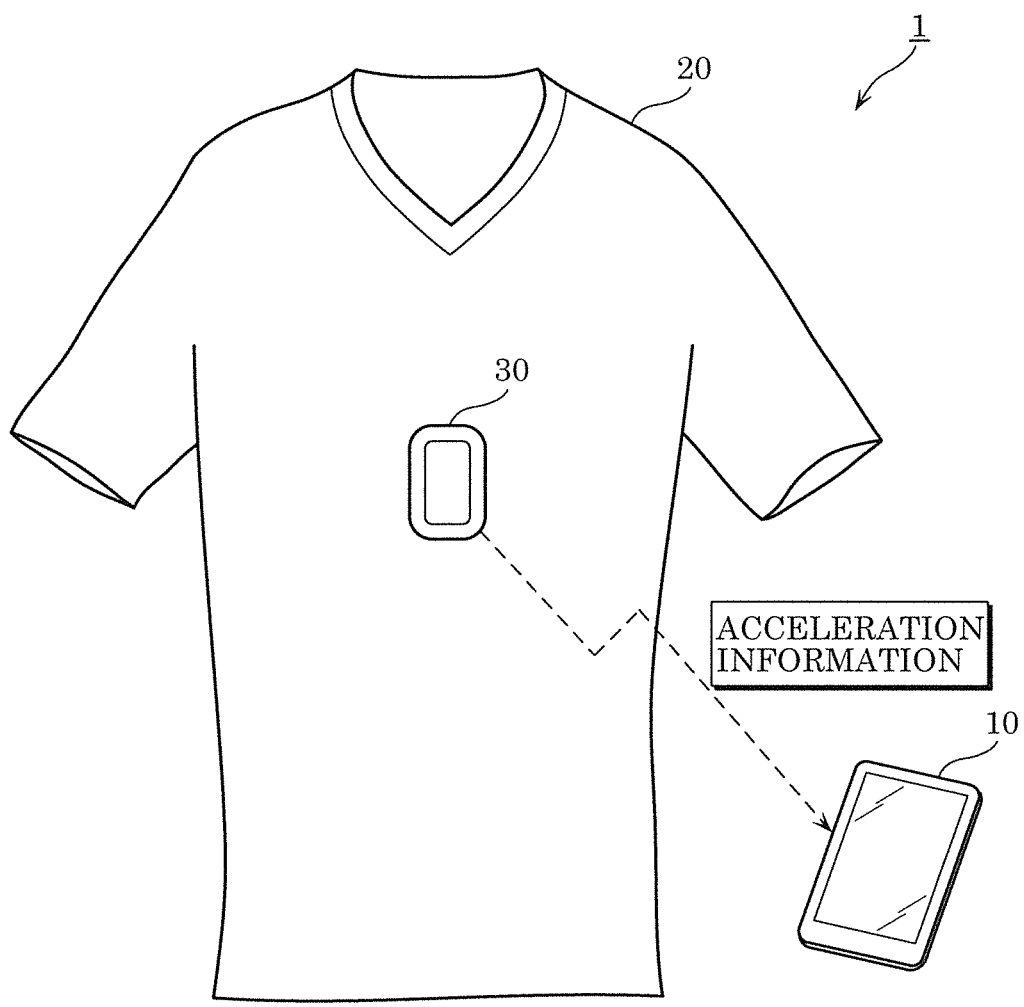
FIG. 1 is a schematic view illustrating an outline of a respiration rate determining system according to Embodiment 1.

FIG. 1 is a schematic view illustrating an outline of a respiration rate determining system according to Embodiment 1.

Specifically, FIG. 1 illustrates respiration rate determining apparatus 10, garment 20, and wearable terminal 30. For example, respiration rate determining system 1 include, among these structural elements, respiration rate determining apparatus 10 and wearable terminal 30. As illustrated in FIG. 1, respiration rate determining apparatus 10 and wearable terminal 30 are separate structurally.

Respiration rate determining system 1 determines a respiration rate of a user by measuring a user's body (chest) movement by the user's respiration.

(1-1-1. Respiration Rate Determining Apparatus)

Figure 2:
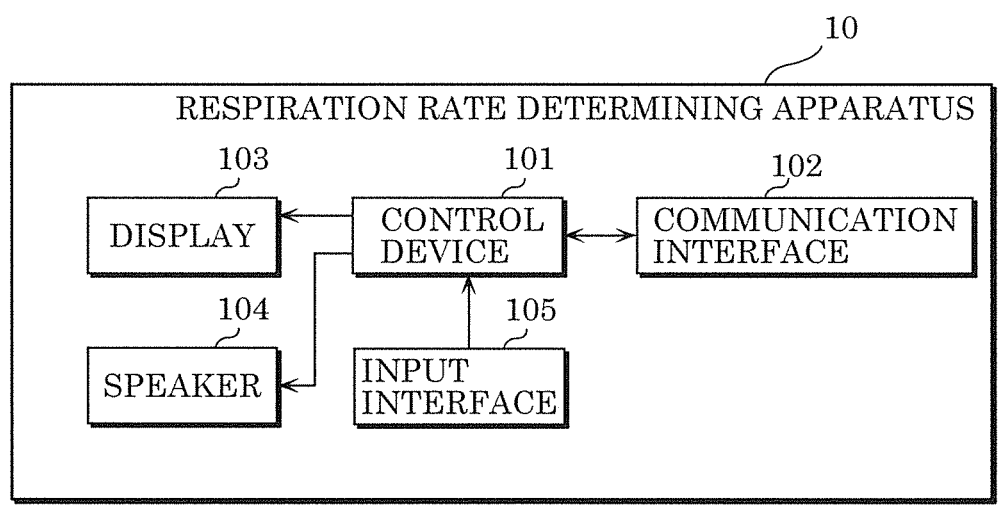
FIG. 2 is a block diagram illustrating an example of a hardware configuration of a respiration rate determining apparatus according to Embodiment 1.

The following describes a hardware configuration of a respiration rate determining apparatus with reference to FIG. 2.

FIG. 2 is a block diagram illustrating an example of a hardware configuration of a respiration rate determining apparatus according to Embodiment 1.

As illustrated in FIG. 2, respiration rate determining apparatus 10 includes control device 101, communication interface (I/F) 102, display 103, speaker 104, and input I/F 105. Respiration rate determining apparatus 10 is, for example, a communicable portable terminal such as a smartphone and a table terminal. It should be noted that although respiration rate determining apparatus 10 is a portable terminal, respiration rate determining apparatus 10 may be a communicable apparatus or an information terminal such as a personal computer (PC).

Control device 101 includes: a processor which executes a control program for causing respiration rate determining apparatus 10 to operate; a volatile storage area (main storage) which is used as a work area when the control program is executed; and an nonvolatile storage area (auxiliary storage) which stores the control program, contents, and so on. Examples of the volatile storage area include a random-access memory (RANI). Examples of the nonvolatile storage area include a read-only memory (ROM), a flash memory, and a hard disk drive (HDD).

Communication I/F 102 communicates with wearable terminal 30. Communication I/F 102 may correspond to communication module 302 (to be described later) included in wearable terminal 30. In other words, communication I/F 102 is, for example, a wireless communication interface compatible with the Bluetooth™ standards. It should be noted that communication I/F 102 may be a wireless local area network (LAN) interface compatible with standards such as IEEE802.11a, IEEE802.11b, IEEE802.11g, and IEEE802.11n, or a wireless communication interface compatible with communications standards used in mobile telecommunications technology such as the third generation of wireless mobile telecommunications technology (3G), the fourth generation of wireless telecommunications technology (4G), and LTE (registered trademark).

Display 103 displays processing results by control device 101. Examples of display 103 include a liquid crystal display and an organic electroluminescence (EL) display.

Speaker 104 outputs sound decoded from audio information.

Input I/F 105 is, for example, a touch panel which is disposed in the surface of display 103 and receives an input to an user interface (UI) displayed on display 103, from a user. Moreover, input I/F 105 may be, for example, an input device such as a numeric keypad and a keyboard.

(1-1-2. Wearable Terminal)

Figure 3:
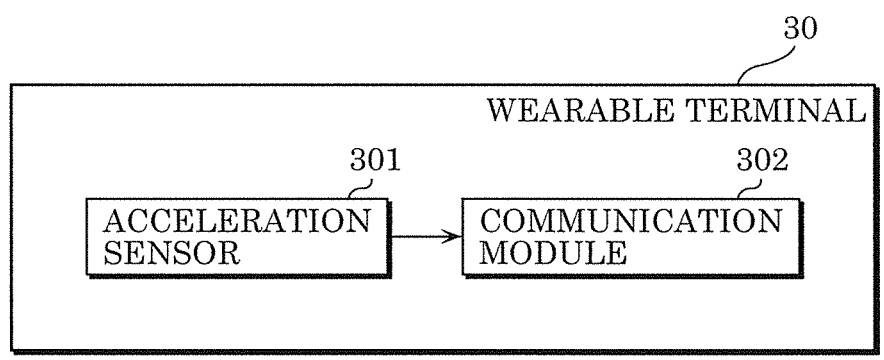
FIG. 3 is a block diagram illustrating an example of a hardware configuration of a wearable terminal according to Embodiment 1.

FIG. 3 is a block diagram illustrating an example of a hardware configuration of a wearable terminal according to Embodiment 1.

As illustrated in FIG. 3, wearable terminal 30 includes acceleration sensor 301 and communication module 302. Wearable terminal 30 is a small terminal which, as illustrated in FIG. 1, is fixed to a location on garment 20 corresponding to the chest of the user, by a snap button, a double-sided tape, an adhesive, a thread, etc. In consequence, wearable terminal 30 is disposed to the chest of the user when the user wears garment 20.

Acceleration sensor 301 measures an acceleration of wearable terminal 30. Specifically, acceleration sensor 301 measures an acceleration of wearable terminal 30 in a direction of each of three axes (X-axis, Y-axis, and Z-axis) orthogonal to one another. It should be noted that in Embodiment 1, a right-left direction, a front-back direction, and an up-down direction relative to the body of the user when the user is in a standing position are defined as the X-axis direction, the Y-axis direction, and the Z-axis direction, respectively. In addition, a positive side of the X-axis direction corresponds to the left side of the right-left direction, a positive side of the Y-axis direction corresponds to the back side of the front-back direction, and a positive side of the Z-axis direction corresponds to the down side of the up-down direction. It should be noted that the directions of the axes are not limited to the above, and it is sufficient that directions make it possible to measure a body movement.

Acceleration sensor 301 detects, as an acceleration, a chest movement by respiration of the user because wearable terminal 30 is disposed to the chest of the user. Wearable terminal 30 measures accelerations along directional axes using acceleration sensor 301 because the chest movement during respiration varies depending on a posture of the user etc. It should be noted that the directional axes need not always be three axes orthogonal to each other, and may be at least two axes in predetermined directions. In other words, acceleration sensor 301 may measure accelerations in directions of at least two axes.

Figure 4:
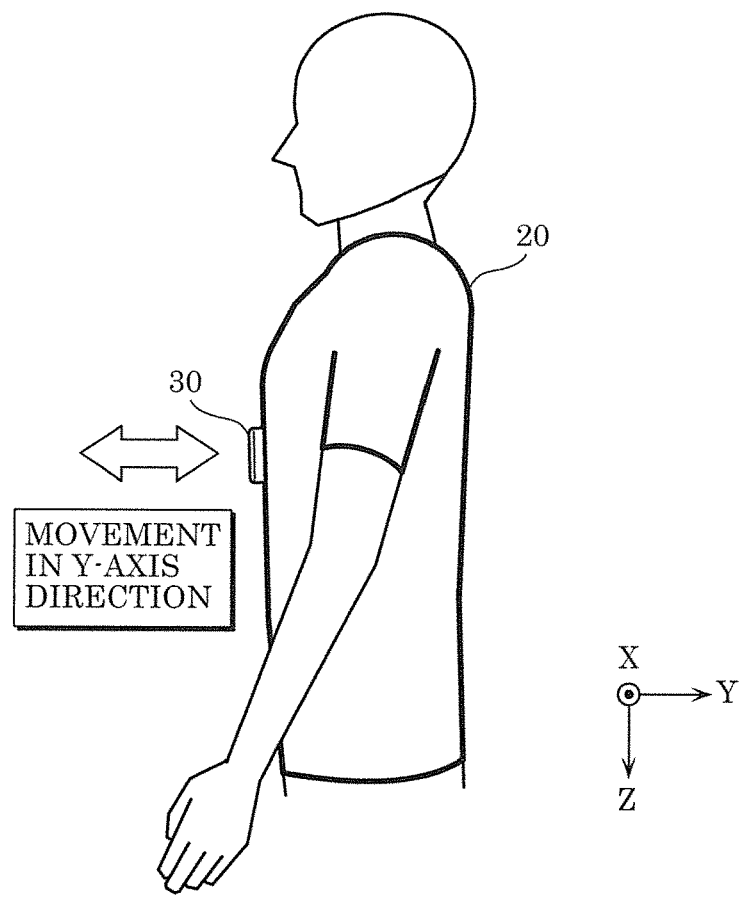
FIG. 4 is a schematic view illustrating a direction of a chest movement accompanied by respiration in the case of a sitting or standing position.

FIG. 4 is a schematic view illustrating a direction of a chest movement accompanied by respiration when the user is in a sitting or standing position.

As illustrated in FIG. 4, when the user is in the sitting or standing position, a chest movement of the user is likely to be in the front-back direction (Y-axis direction) relative to the user. For this reason, when the user is in the sitting or standing position, acceleration sensor 301 detects the chest movement accompanied by respiration, using an acceleration in the Y-axis direction.

Figure 5:
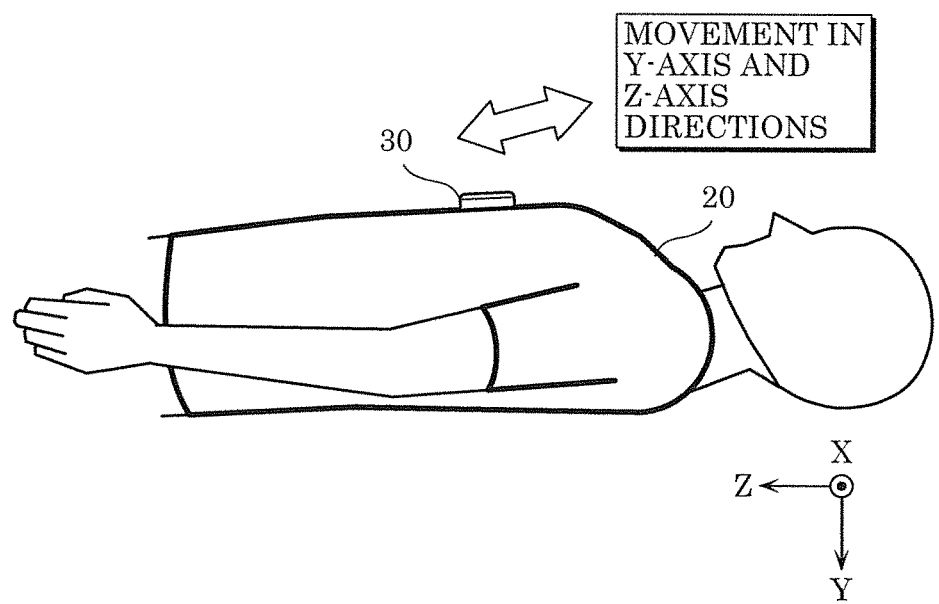
FIG. 5 is a schematic view illustrating a direction of a chest movement accompanied by respiration in the case of a supine position.

FIG. 5 is a schematic view illustrating a direction of a chest movement accompanied by respiration when the user is in a supine position.

As illustrated in FIG. 5, when the user is in the supine position, the chest movement of the user includes many motions in the up-down direction (Z-axis direction) relative to the user in addition to motions in the front-back direction (Y-axis direction) relative to the user. For this reason, when the user is in the supine position, acceleration sensor 301 detects the chest movement accompanied by respiration, using accelerations in the Y-axis direction and the Z-axis direction.

Acceleration sensor 301 of wearable terminal 30 measures accelerations along directional axes because the chest movement accompanied by the user's respiration differs depending on the user's posture as stated above.

Communication module 302 communicates with respiration rate determining apparatus 10. Communication module 302 may include, for example, a wireless communication interface compatible with the Bluetooth™ standards or a wireless local area network (LAN) interface compatible with standards such as IEEE802.11a, IEEE802.11b, IEEE802.11g, and IEEE802.11n.

1-2. Functional Configuration of Respiration Rate Determining System

Figure 6:
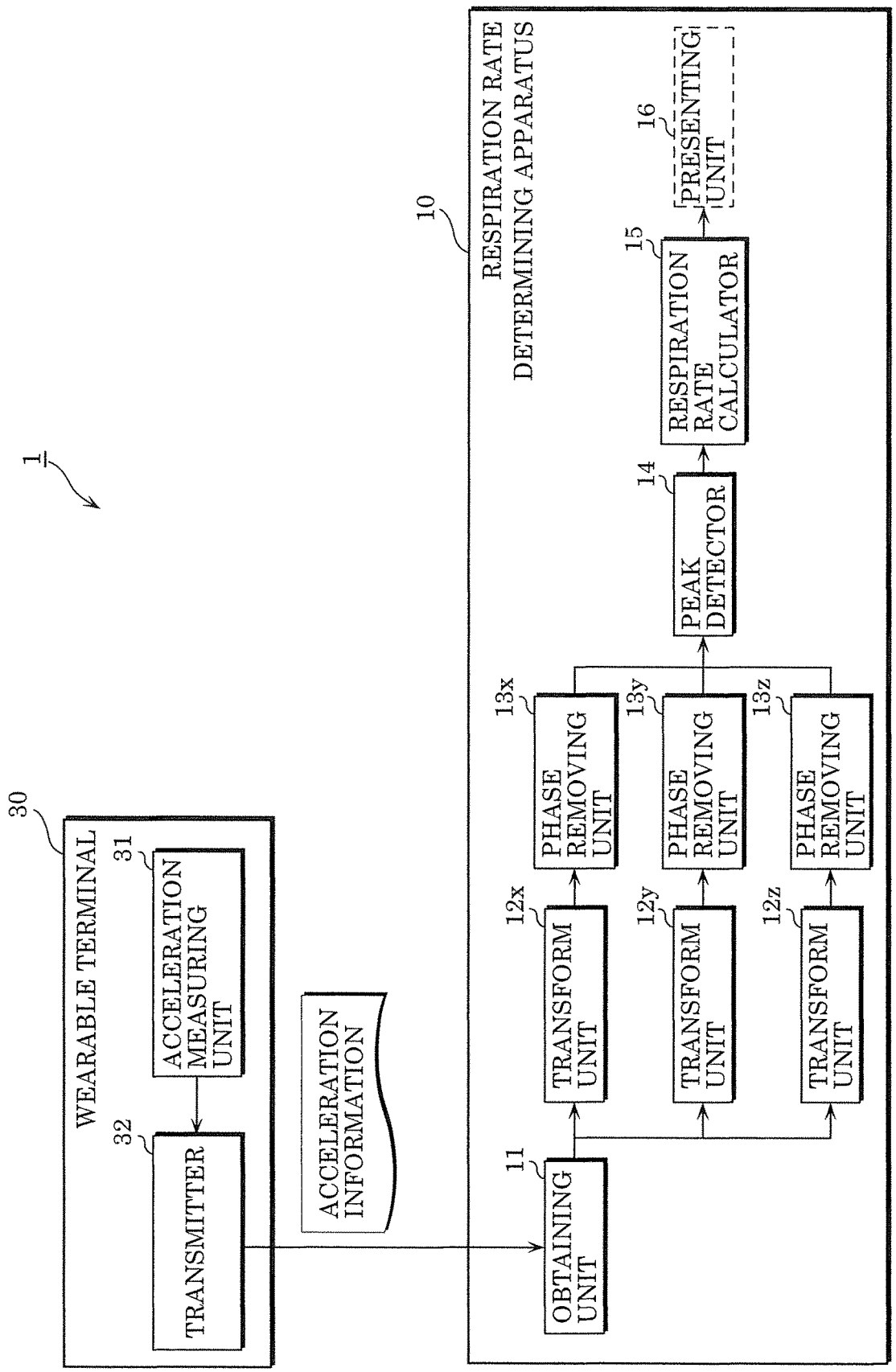
FIG. 6 is a block diagram illustrating an example of a functional configuration of the respiration rate determining system according to Embodiment 1.

The following describes a functional configuration of respiration rate determining system 1 with reference to FIG. 6.

FIG. 6 is a block diagram illustrating an example of a functional configuration of a respiration rate determining system according to Embodiment 1.

First, a functional configuration of wearable terminal 30 will be described.

Wearable terminal 30 includes, as functional elements, acceleration measuring unit 31 and transmitter 32.

Acceleration measuring unit 31 measures a body movement by the user's respiration, in accelerations in mutually different directions. Acceleration measuring unit 31 measures accelerations in directions using a predetermined sampling frequency, and generates acceleration information indicating a time series variation in acceleration in each direction. Acceleration measuring unit 31 is implemented by, for example, acceleration sensor 301.

Transmitter 32 transmits the generated acceleration information to respiration rate determining apparatus 10. It should be noted that transmitter 32 transmits acceleration information stored in a memory not shown to respiration rate determining apparatus 10 on a predetermined cycle. Transmitter 32 is implemented by, for example, communication module 302. In other words, transmitter 32 transmits acceleration information to respiration rate determining apparatus 10 connected for communication based on, for example, Bluetooth™.

Next, a functional configuration of respiration rate determining apparatus 10 will be described.

Respiration rate determining apparatus 10 includes obtaining unit 11, transform units 12$x$, 12$y$, and 12$z$, phase removing units 13$x$, 13$y$, and 13$z$, peak detector 14, and respiration rate calculator 15. Respiration rate determining apparatus 10 may further include presenting unit 16.

Obtaining unit 11 receives acceleration information transmitted by transmitter 32 of wearable terminal 30. In other words, obtaining unit 11 communicates with wearable terminal 30 including acceleration sensor 301 and attached to the user's body. Consequently, obtaining unit 11 obtains acceleration information indicating accelerations in mutually different directions obtained by acceleration sensor 301 measuring a body movement by the user's respiration. Obtaining unit 11 is implemented by, for example, control device 101 and communication I/F 102.

Transform units 12$x$, 12$y$, and 12$z$ transform the accelerations in the directions indicated in the acceleration information obtained by obtaining unit 11, into spectrum information items. Transform unit 12$x$ performs the transformation on the acceleration in the X-axis direction. Transform unit 12$y$ performs the transformation on the acceleration in the Y-axis direction. Transform unit 12$z$ performs the transformation on the acceleration in the Z-axis direction. Transform units 12$x$, 12$y$, and 12$z$ transform, using the fast Fourier transform (FFT), acceleration values in respective directions into spectrum information items in a frequency domain of the respective directions. In other words, the transformation makes it possible to obtain the spectrum information items in the respective directions, that is, three spectrum information items.

Transform units 12$x$, 12$y$, and 12$z$ are not particularly limited, and may perform the FFT for a duration (approximately from two to twenty seconds) of, for example, approximately one to ten respiration periods. It should be noted that the duration indicates a period in which the FFT is repeated. Here, when the duration in which the FFT is performed is reduced, conformity to a variation in respiration rate is enhanced, but sensitivity to noise such as a body movement other than respiration is increased. In contrast, when the duration is extended, the sensitivity to noise such as a body movement other than respiration is decreased, but the conformity to the variation in respiration rate is reduced. Accordingly, it is desirable that the duration in which the FFT is performed be appropriately adjusted. Moreover, it is desirable that a window function such as a hanning window be used when the FFT is performed.

Transform units 12$x$, 12$y$, and 12$z$ are implemented by, for example, control device 101.

Phase removing units 13$x$, 13$y$, and 13$z$ extract amplitude spectra by removing phase information from spectrum information items transform units 12$x$, 12$y$, and 12$z$ transformed into a frequency domain. Phase removing unit 13$x$ transforms the spectrum information in the X-axis direction into an amplitude spectrum by removing phase information from the spectrum information in the X-axis direction. Phase removing unit 13$y$ transforms the spectrum information in the Y-axis direction into an amplitude spectrum by removing phase information from the spectrum information in the Y-axis direction. Phase removing unit 13$z$ transforms the spectrum information in the Z-axis direction into an amplitude spectrum by removing phase information from the spectrum information in the Z-axis direction. In other words, phase removing units 13$x$, 13$y$, and 13$z$ transform the spectrum information items in the respective directions into the amplitude spectra in the respective directions by removing the phase information from the spectrum information items in the frequency domain in the respective directions. The transformation makes it possible to obtain the amplitude spectra in the respective directions, that is, three amplitude spectra. Accordingly, it is possible to remove a phase difference among the movement components of respiration included in the accelerations in the respective directions. Phase removing units 13$x$, 13$y$, and 13$z$ are implemented by, for example, control device 101.

Peak detector 14 superimposes, on one another, the respiratory components in the respective directions by adding up the three amplitude spectra from which phase removing units 13$x$, 13$y$, and 13$z$ removed the phase information. Subsequently, peak detector 14 detects, as peak frequency Fp, a frequency having a peak value of an amplitude spectrum resulting from the superimposition, based on the amplitude spectrum. Peak detector 14 may detect peak frequency Fp of the amplitude spectrum in a frequency band that is preset as a detection range. For example, assuming that the number of breaths per minute is 5 to 30, peak detector 14 may detect peak frequency Fp in a detection range of from 0.08 (Hz) to 0.5 (Hz), inclusive. By setting the detection range in which peak frequency Fp is detected as above, peak detector 14 is capable of preventing false detection when noise is found outside of the detection range. Peak detector 14 is implemented by, for example, control device 101.

Respiration rate calculator 15 calculates respiration rate Rc (breaths per minute: bpm) using peak frequency Fp (Hz) of the amplitude spectrum of the accelerations detected by peak detector 14. Respiration rate calculator 15 is implemented by, for example, control device 101.

Presenting unit 16 displays an image or character information indicating the respiration rate calculated by respiration rate calculator 15. Presenting unit 16 may output voice indicating the calculated respiration rate. Presenting unit 16 may be implemented by, for example, control device 101 and display 103 or control device 101 and speaker 104.

1-3. Operation

Figure 7:
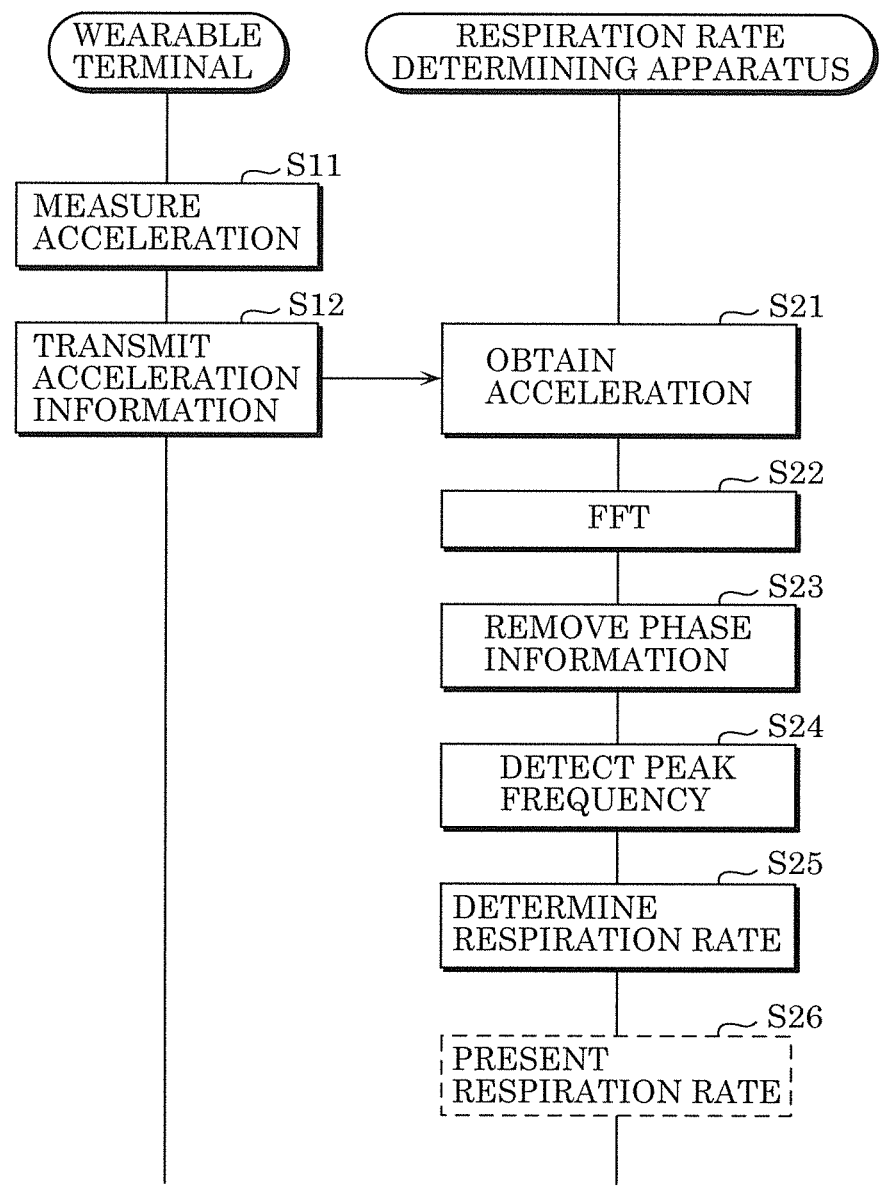
FIG. 7 is a sequence diagram illustrating an example of operation performed by the respiration rate determining system according to Embodiment 1.

The following describes operation performed by respiration rate determining system 1 thus configured with reference to FIG. 7. Specifically, a respiration rate determining method performed by respiration rate determining system 1 will be described.

FIG. 7 is a sequence diagram illustrating an example of a respiration rate determining method performed by the respiration rate determining system according to Embodiment 1.

Wearable terminal 30 attached to the user's body as illustrated in FIG. 4 and FIG. 5 causes acceleration measuring unit 31 to measure a chest movement of the user as triaxial accelerations (S11).

Figure 8:
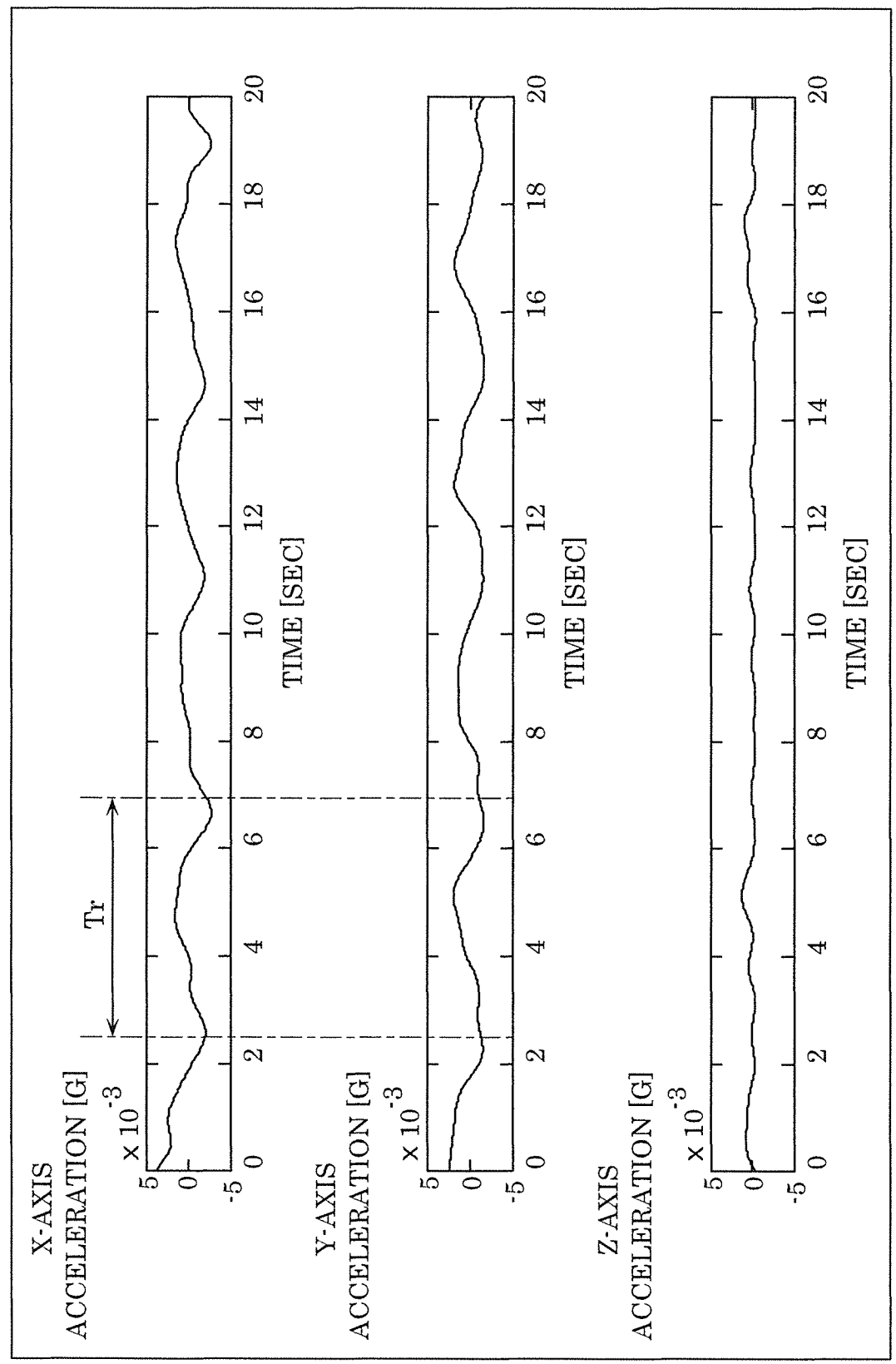
FIG. 8 is a graph illustrating accelerations measured by a triaxial acceleration sensor according to Embodiment 1.

FIG. 8 is a graph illustrating an example of the triaxial accelerations (acceleration information) measured by the acceleration measuring unit. In FIG. 8, the horizontal axis represents time, and the vertical axis represents acceleration. In FIG. 8, movement components by respiration are mainly included in the acceleration in the X-axis direction and the acceleration in the Y-axis direction. It is clear from FIG. 8 that cycle Tr is approximately four seconds (0.25 (Hz)).

Next, wearable terminal 30 causes transmitter 32 to transmit the acceleration information to respiration rate determining apparatus 10 (S12).

Subsequently, respiration rate determining apparatus 10 obtains the accelerations in the respective directions indicated by the acceleration information, by causing obtaining unit 11 to receive the acceleration information from transmitter 32 of wearable terminal 30 (S21).

Next, transform units 12$x$, 12$y$, and 12$z$ transform, using the FFT, the obtained accelerations in the respective directions into spectrum information items in a frequency domain (S22). Specifically, transform unit 12$x$ transforms, using the FFT, acceleration $x_n$ in the X-axis direction into spectrum information $X_k$ in a frequency domain, using Equation 1a. Transform unit 12$y$ transforms, using the FFT, acceleration $y_n$ in the Y-axis direction into spectrum information $Y_k$ in a frequency domain, using Equation 1b. Transform unit 12$z$ transforms, using the FFT, acceleration $z_n$ in the Z-axis direction into spectrum information $Z_k$ in a frequency domain, using Equation 1c.

[Math. 1]

$$X_k = \sum_{n=0}^{N-1} x_n e^{-i\frac{2\pi nk}{N}} \quad \text{(Equation 1a)}$$

$$Y_k = \sum_{n=0}^{N-1} y_n e^{-i\frac{2\pi nk}{N}} \quad \text{(Equation 1b)}$$

$$Z_k = \sum_{n=0}^{N-1} z_n e^{-i\frac{2\pi nk}{N}} \quad \text{(Equation 1c)}$$

In Equation 1a to Equation 1c, N denotes the number of points at which the FFT is performed, n denotes a sample number, and k denotes an index of the FFT.

Next, phase removing units 13$x$, 13$y$, and 13$z$ remove phase information from the spectrum information items $X_k$, $Y_k$, and $Z_k$ in the frequency domain in the respective directions (S23). Specifically, phase removing unit 13$x$ calculates amplitude spectrum $AX_k$ that is an absolute value, by removing phase information from spectrum information $X_k$ obtained by transforming acceleration $x_n$ in the X-axis direction into a frequency domain using Equation 2a. Phase removing unit 13$y$ calculates amplitude spectrum $AY_k$ that is an absolute value, by removing phase information from spectrum information $Y_k$ obtained by transforming acceleration $y_n$ in the Y-axis direction into a frequency domain using Equation 2b. Phase removing unit 13$z$ calculates amplitude spectrum $AZ_k$ that is an absolute value, by removing phase information from spectrum information $Z_k$ obtained by transforming acceleration $z_n$ in the Z-axis direction into a frequency domain using Equation 2c.

[Math. 2]

$$AX_k = |X_k| \quad \text{(Equation 2a)}$$

$$AY_k = |Y_k| \quad \text{(Equation 2b)}$$

$$AZ_k = |Z_k| \quad \text{(Equation 2c)}$$

Figure 9:
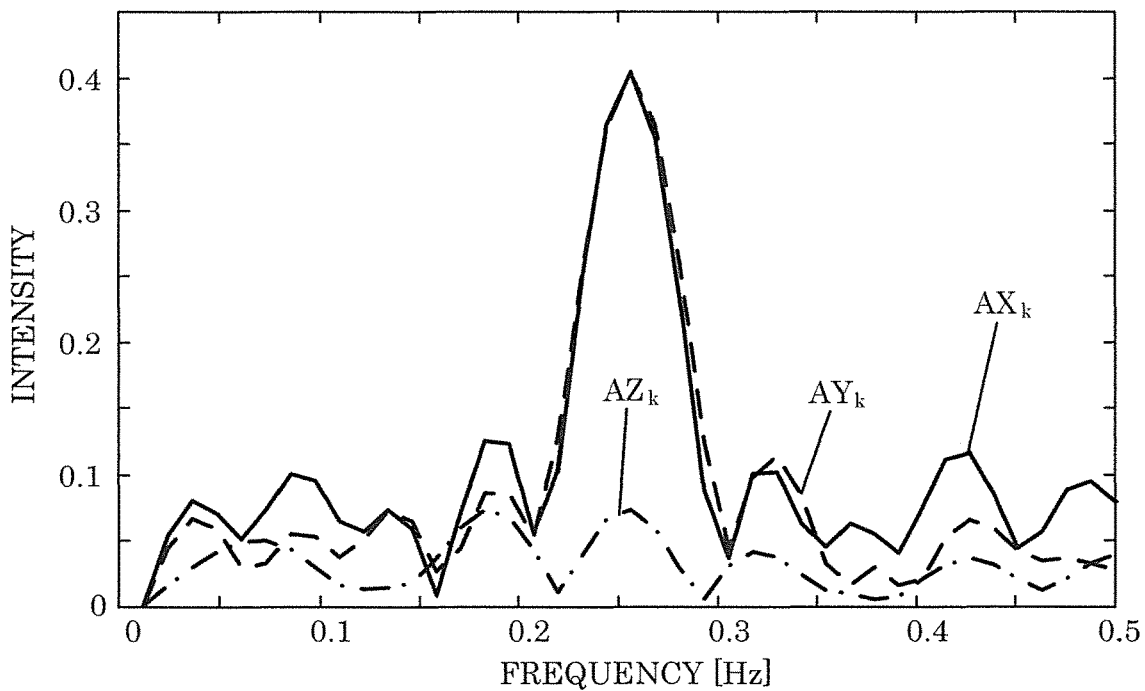
FIG. 9 is a graph illustrating an amplitude spectrum in each direction in Embodiment 1.

FIG. 9 is a graph illustrating amplitude spectra in respective directions calculated from the accelerations in the respective directions illustrated in FIG. 8. In FIG. 9, the horizontal axis represents frequency, and the vertical axis represents intensity. In FIG. 9, a solid line, a broken line, and a dashed line represent amplitude spectrum $AX_k$ in the X-axis direction, amplitude spectrum $AY_k$ in the Y-axis direction, and amplitude spectrum $AZ_k$ in the Z-axis direction, respectively. It is clear from FIG. 9 that many respiratory components in the proximity of frequency 0.25 (Hz) are included in, among amplitude spectra $AX_k$, $AY_k$, and $AZ_k$ in the respective directions, amplitude spectrum $AX_k$ in the X-axis direction and amplitude spectrum $AY_k$ in the Y-axis direction.

Next, peak detector 14 adds up amplitude spectra $AX_k$, $AY_k$, and $AZ_k$ in the respective directions as indicated in Equation 3, and calculates peak frequency Fp having a peak value of amplitude spectrum $A_k$ resulting from the adding up, using Equation 4 and Equation 5 (S24).

[Math. 3]

$$A_k = AX_k + AY_k + AZ_k \quad \text{(Equation 3)}$$

[Math. 4]

$$\hat{k} = \text{argmax}_k A_k \quad \text{(Equation 4)}$$

[Math. 5]

$$Fp = \frac{\hat{k}}{N} Fs [\text{Hz}] \quad \text{(Equation 5)}$$

Here, argmax_k denotes a function that calculates k maximizing $A_k$, and Fs denotes a sampling frequency for measurement by acceleration sensor 301.

Sampling frequency Fs is not particularly limited, but it is desirable that sampling frequency Fs be sufficiently greater than the upper limit (several Hz) of a respiratory frequency.

Figure 10:
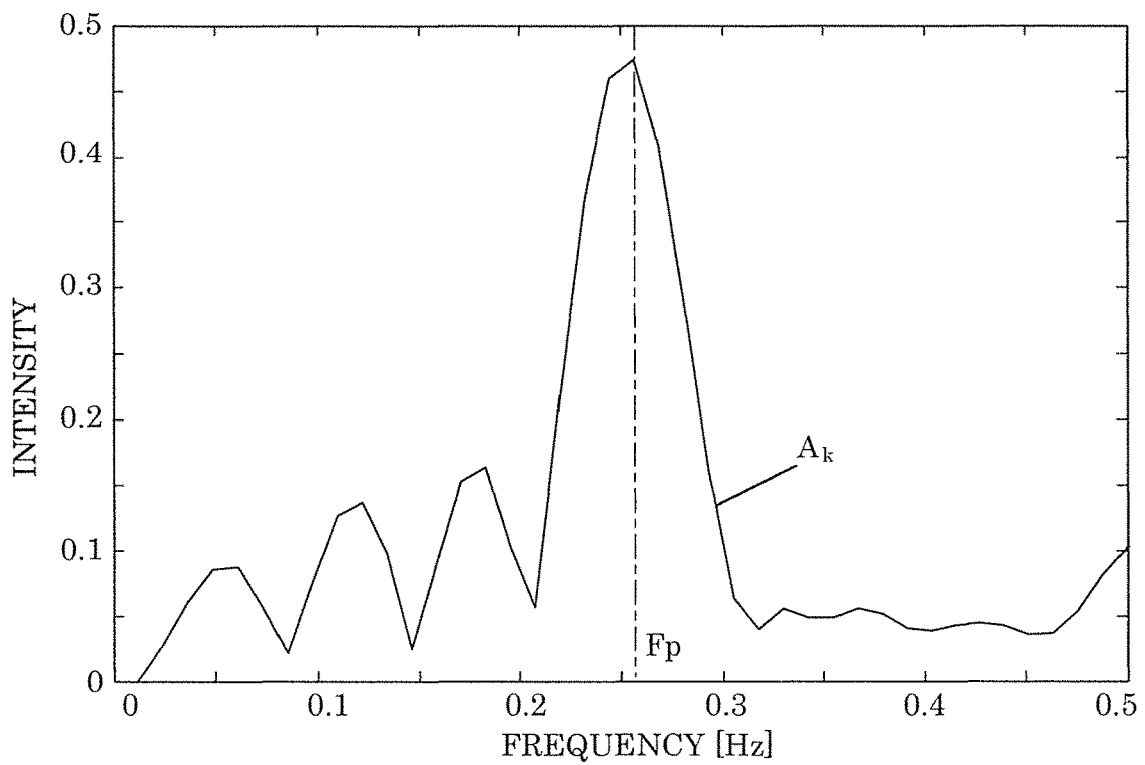
FIG. 10 is a graph illustrating an amplitude spectrum combined in Embodiment 1.

FIG. 10 is a graph illustrating amplitude spectrum $A_k$ resulting from combining (adding up) the amplitude spectra in the respective directions. In FIG. 10, the horizontal axis represents frequency, and the vertical axis represents intensity. Combined amplitude spectrum $A_k$ has peak frequency Fp in the proximity of 0.25 Hz that is a respiratory frequency. It is possible to accurately determine a respiration rate of the user by calculating peak frequency Fp.

Next, respiration rate calculator 15 calculates respiration rate Rc per minute (bpm) using calculated peak frequency Fp and Equation 6 (S25).

[Math. 6]

$$Rc = Fp \times 60 \ [\text{bpm}] \quad \text{(Equation 6)}$$

In the example of FIG. 10, respiration rate Rc is approximately 15 (times/minute) because peak frequency Fp is in the proximity of 0.25 (Hz).

Accordingly, when the accelerations including the respiratory components measured by acceleration sensor 301 are added up and the respiration rate is calculated, even if a phase difference among the respiratory components caused by the user's posture or the like is present, it is possible to reduce the influence of the phase difference, thereby stably determining the respiration rate.

As a comparative example, a case will be described in which synthetic acceleration G of accelerations along directional axes at a time is calculated using Equation 7, and a respiration rate is calculated from synthetic acceleration G.

[Math. 7]

$$G = \sqrt{x^2 + y^2 + z^2} \ [G] \quad \text{(Equation 7)}$$

Here, x, y, and z denote accelerations in the X-axis, Y-axis, and Z-axis directions at a time, respectively, and G denotes an acceleration resulting from combining x, y, and z.

It is possible to combine respiratory components included in the respective directions using synthetic acceleration G. However, when a phase difference among movement components of respiration included in accelerations in respective directions arises from the user's posture, a state of respiration, etc., synthetic acceleration G may indicate a movement other than the respiratory components.

An example in which synthetic acceleration G of the accelerations in the X-axis, Y-axis, and Z-axis directions illustrated in FIG. 8 is calculated using Equation 7 will be described with reference to FIG. 11.

Figure 11:
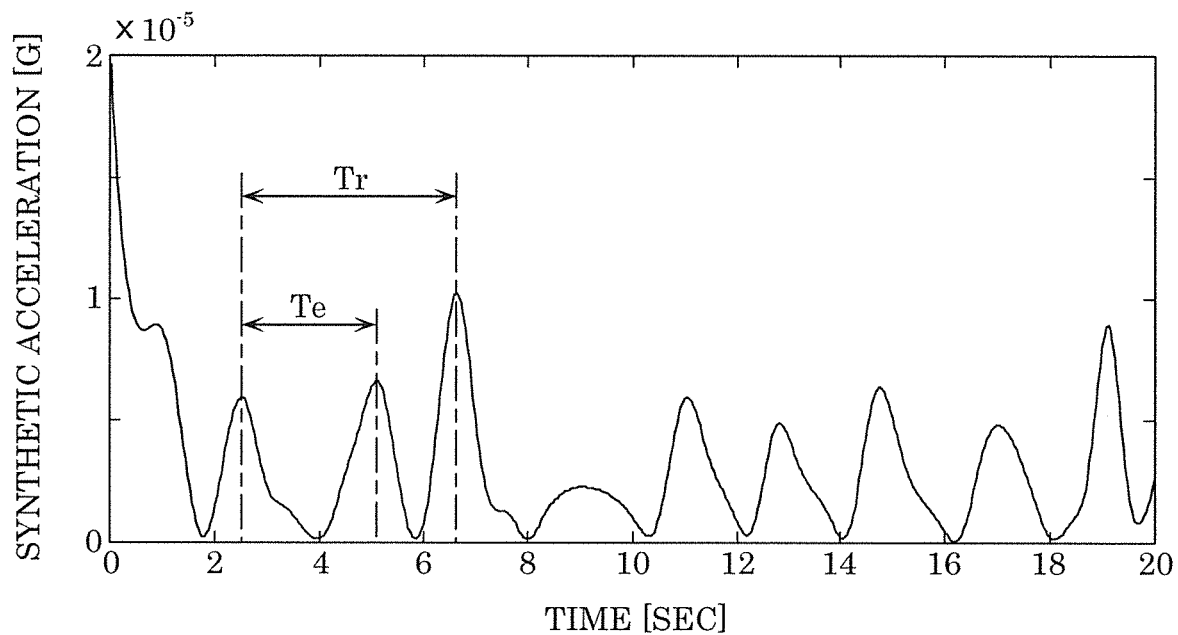
FIG. 11 is a graph illustrating a synthetic acceleration according to a comparative example.

FIG. 11 is a graph illustrating a synthetic acceleration according to the comparative example. In FIG. 11, the horizontal axis represents time, and the vertical axis represents synthetic acceleration G.

As illustrated in FIG. 11, synthetic acceleration G indicates cycle Tr of the respiratory components included in the accelerations in the X-axis, Y-axis, and Z-axis directions, and cycle Te of components. As above, when synthetic acceleration G is used in Equation 7, fake peaks other than the respiratory components may appear because the influence of the posture etc. makes a phase of a variation in acceleration in each direction different.

Figure 12:
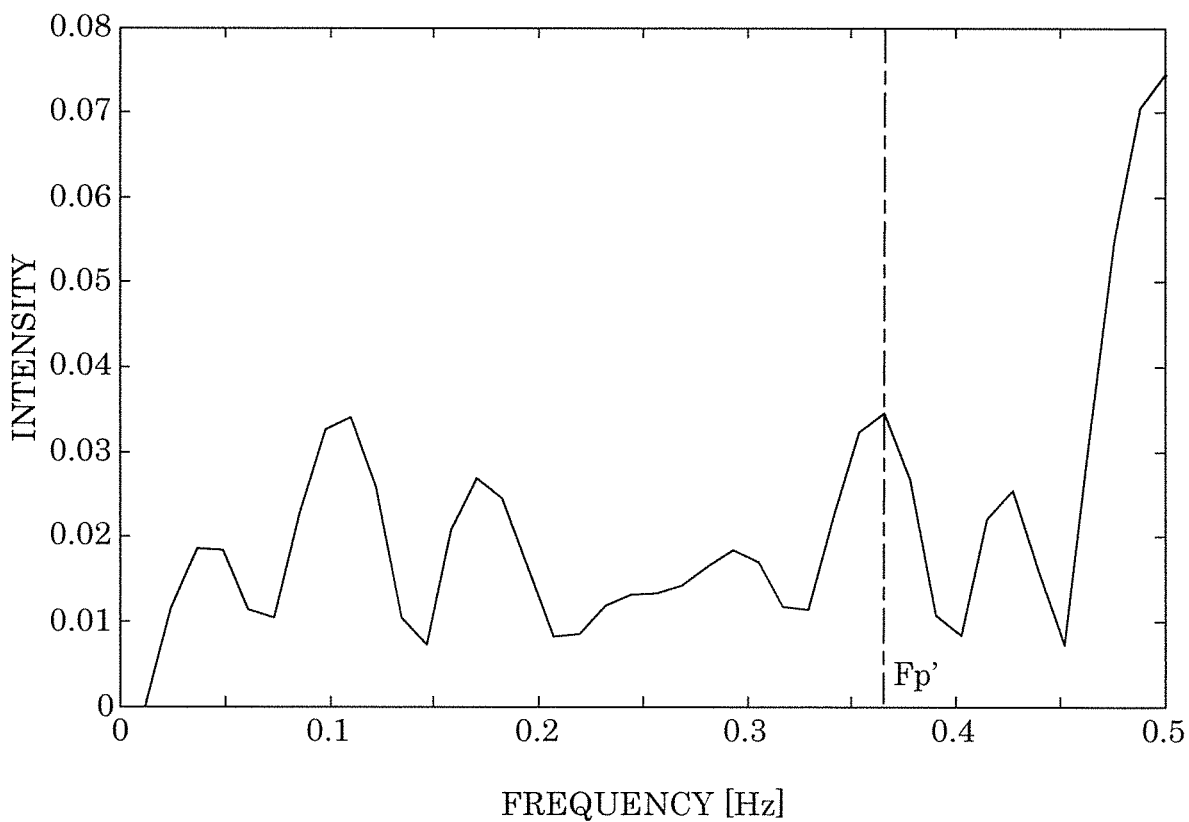
FIG. 12 is a graph illustrating an amplitude spectrum based on the synthetic acceleration according to the comparative example.

An amplitude spectrum of synthetic acceleration G indicated in Equation 7 will be further examined with reference to FIG. 12.

FIG. 12 is a graph illustrating an amplitude spectrum based on the synthetic acceleration according to the comparative example. In FIG. 12, the horizontal axis represents frequency, and the vertical axis represents intensity. The amplitude spectrum of synthetic acceleration G has peak frequency Fp' in the proximity of 0.37 Hz. In addition, the amplitude spectrum of synthetic acceleration G has no clear peak in the proximity of 0.25 Hz that is the natural respiratory frequency.

According to Equation 6, respiration rate Rc' is approximately 22 (times/minute) because peak frequency Fp' is in the proximity of 0.37 (Hz). As above, when synthetic acceleration G calculated by Equation 7 is used, there are cases where a respiratory frequency is falsely detected because a phase difference occurs in time series data of accelerations in respective directions due to the user's posture or the like.

1-4. Advantageous Effects Etc

As described above, respiration rate determining apparatus 10 includes obtaining unit 11, transform processors 12x, 12y, and 12z, phase removing units 13x, 13y, and 13z, peak detector 14, and respiration rate calculator 15. Obtaining unit 11 obtains accelerations in directions that are mutually different, the accelerations being obtained by acceleration sensor 301 measuring a body movement by respiration of a user. Transform units 12x, 12y, and 12z transform the accelerations in the directions obtained by obtaining unit 11, into spectrum information items in a frequency domain. Phase removing units 13x, 13y, and 13z transform the spectrum information items into amplitude spectra by removing phase information from the spectrum information items. Peak detector 14 adds up the amplitude spectra and detects peak frequency Fp based on an amplitude spectrum resulting from the adding up, peak frequency Fp indicating a respiratory component. Respiration rate calculator 15 calculates a respiration rate using peak frequency Fp.

With this, even if a phase difference among respiratory components caused by a user's posture or the like is present in accelerations including the respiratory components measured by acceleration sensor 301, it is possible to stably determine a respiration rate.

It should be noted that although wearable terminal 30 is fixed to the chest of garment 20 in Embodiment 1, the present disclosure is not limited to this, and wearable terminal 30 may be fixed to a position at which a body movement accompanied by person's respiration can be measured, such as the abdominal region of the person.

Embodiment 2

Hereinafter, Embodiment 2 will be described with reference to FIG. 13 through FIG. 15.

2-1. Configuration

Figure 13:
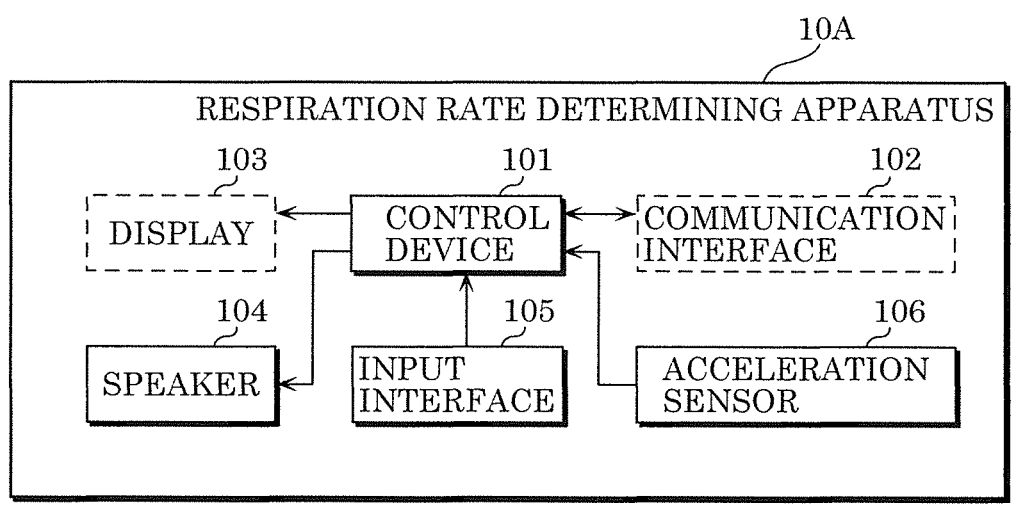
FIG. 13 is a block diagram illustrating an example of a hardware configuration of a respiration rate determining apparatus according to Embodiment 2.

FIG. 13 is a block diagram illustrating an example of a hardware configuration of a respiration rate determining apparatus according to Embodiment 2.

As illustrated in FIG. 13, unlike Embodiment 1, respiration rate determining apparatus 10A performs all steps in a respiration rate determining method in Embodiment 2. In other words, respiration rate determining apparatus 10A according to Embodiment 2 differs from respiration rate determining apparatus 10 according to Embodiment 1 in further including acceleration sensor 106. Acceleration sensor 106 has the same configuration as acceleration sensor 301. Since the other structural elements are the same as in Embodiment 1, the same reference signs are assigned thereto, and descriptions thereof are omitted.

In Embodiment 2, respiration rate determining apparatus 10A needs not include display 103 and communication I/F 102. In addition, respiration rate determining apparatus 10A is implemented by a small terminal fixed to garment 20 illustrated in FIG. 1.

Figure 14:
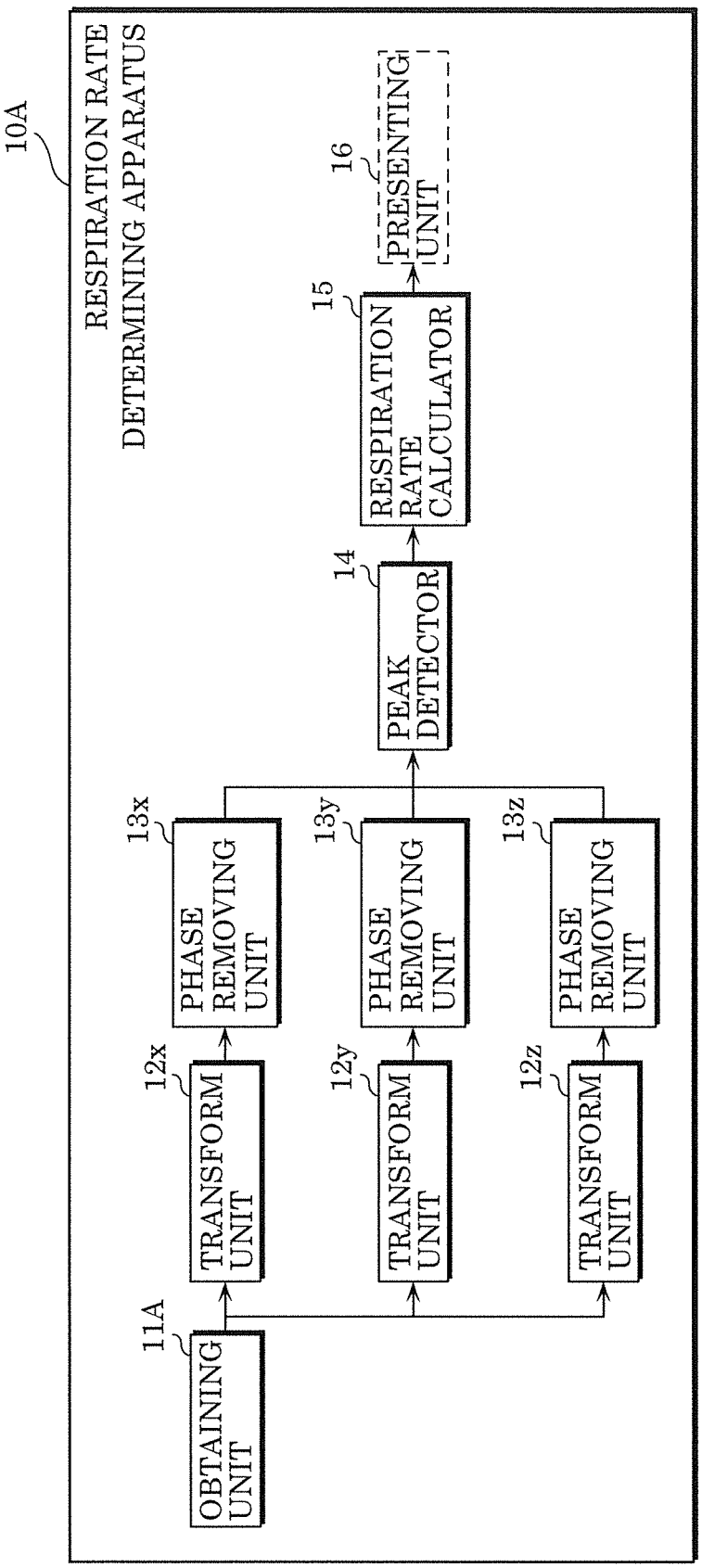
FIG. 14 is a block diagram illustrating an example of a functional configuration of the respiration rate determining apparatus according to Embodiment 2.

FIG. 14 is a block diagram illustrating an example of a functional configuration of the respiration rate determining apparatus according to Embodiment 2.

As illustrated in FIG. 14, unlike Embodiment 1, obtaining unit 11A is implemented by acceleration sensor 106 in Embodiment 2. In other words, obtaining unit 11A measures a body movement by the user's respiration, in accelerations in mutually different directions.

Since structural elements other than obtaining unit 11A are the same as in Embodiment 1, the same reference signs are assigned thereto, and descriptions thereof are omitted.

2-2. Operation

Figure 15:
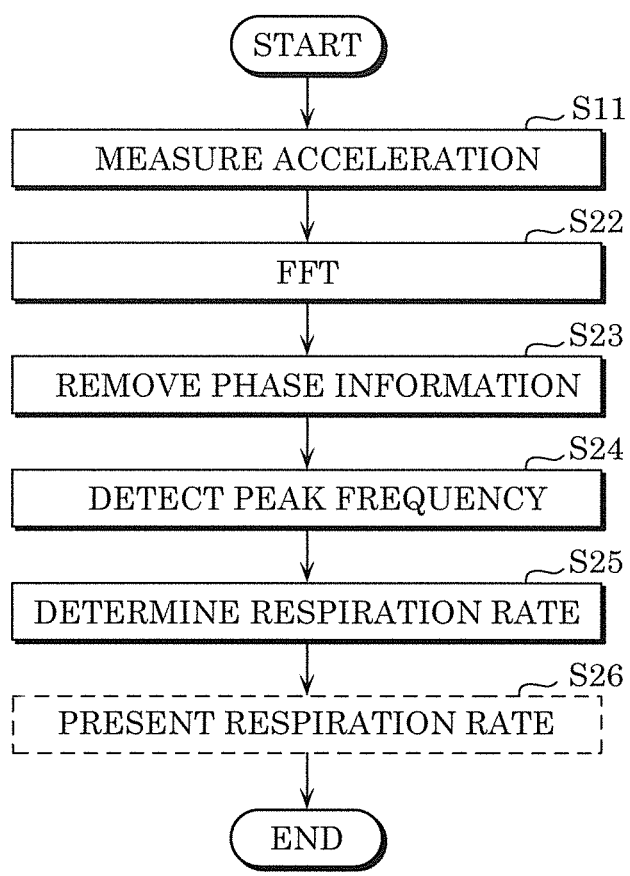
FIG. 15 is a flow chart illustrating operation performed by the respiration rate determining apparatus according to Embodiment 2.

FIG. 15 is a flow chart illustrating an example of the respiration rate determining method performed by the respiration rate determining apparatus according to Embodiment 2.

As illustrated in FIG. 15, the operation of respiration rate determining apparatus 10A according to Embodiment 2 differs from the operation of respiration rate determining system 1 according to Embodiment 1 in that respiration rate determining apparatus 10A completes an entire process. In other words, steps S12 and S21 are omitted from the sequence diagram illustrated in FIG. 7.

To put it differently, respiration rate determining apparatus 10A performs step S22 after performing step S11. Accordingly, respiration rate determining apparatus 10A obtains accelerations, performs transformation (the FFT), removes phase information, detects a peak frequency, and calculates a respiration rate.

It should be noted that the above embodiments are examples of the techniques of the present disclosure, and thus various modifications, permutations, additions, omissions, etc. are possible within the scope of the appended claims or the equivalents thereof.

It should be noted that transformation into a frequency domain is not limited to the FFT, and may be the discrete Fourier transform (DFT), the discrete cosine transform (DCT), wavelet transform, etc.

Respiration rate Rc thus calculated may be transmitted via a network to a server not shown. Alternatively, respiration rate Rc thus calculated may be accumulated in a storage not shown.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

A respiration rate determining apparatus, a respiration rate determining method, and a program recording medium according to the present disclosure make it possible to accurately determine a respiration rate regardless of a state of a user such as a posture, and thus are useful as a respiration rate determining apparatus, a respiration rate determining method, a program recording medium, etc. which determine a respiration rate from measured data of an acceleration sensor attached to the user's body.

What is claimed is:

1. A respiration rate determining apparatus, comprising:
a memory configured to store a program;
one or more processors configured to execute the program and control the respiration rate determining apparatus to:
obtain accelerations in directions that are mutually different, measure a body movement by respiration of a user;
transform the accelerations in the directions obtained into spectrum information items in a frequency domain;
transform the spectrum information items into amplitude spectra by removing phase information from the spectrum information items;
add up the amplitude spectra and detect a peak frequency based on an amplitude spectrum resulting from the adding up, the peak frequency indicating a respiratory component; and
calculate a respiration rate using the peak frequency.

2. The respiration rate determining apparatus according to claim 1,
wherein the one or more processors are further configured to execute the program and control the respiration rate determining apparatus to transform each of the accelerations in the directions into a corresponding one of the spectrum information items, using fast Fourier transform.

3. The respiration rate determining apparatus according to claim 1,
wherein the one or more processors are further configured to execute the program and control the respiration rate determining apparatus to perform the transformation for a duration of one to ten respiration periods.

4. The respiration rate determining apparatus according to claim 1,
wherein the one or more processors are further configured to execute the program and control the respiration rate determining apparatus to detect the peak frequency in a detection range of from 0.08 Hz to 0.5 Hz, inclusive.

5. The respiration rate determining apparatus according to claim 1,
wherein the one or more processors are further configured to execute the program and control the respiration rate determining apparatus to obtain the accelerations in the directions from a terminal attached to a body of the user, by communicating with the terminal, and
the respiration rate determining apparatus is structurally separate from the terminal.

6. The respiration rate determining apparatus according to claim 1,
   wherein
   the respiration rate determining apparatus obtains the accelerations, performs the transformation, removes the phase information, detects the peak frequency, and calculates the respiration rate.

* * * * *